(12) United States Patent
Zeng et al.

(10) Patent No.: US 9,804,083 B2
(45) Date of Patent: Oct. 31, 2017

(54) OPTICAL STANDARD FOR CALIBRATION OF SPECTRAL MEASURING SYSTEMS

(71) Applicants: Verisante Technology, Inc., Richmond (CA); British Columbia Cancer Agency Branch, Vancouver (CA)

(72) Inventors: Haishan Zeng, Vancouver (CA); Hequn Wang, Belmont, MA (US); Thomas Andrew Braun, Richmond (CA)

(*) Notice: Subject to any disclaimer, the term of this patent is extended or adjusted under 35 U.S.C. 154(b) by 42 days.

(21) Appl. No.: 14/766,439

(22) PCT Filed: Feb. 11, 2014

(86) PCT No.: PCT/CA2014/050094
§ 371 (c)(1),
(2) Date: Aug. 6, 2015

(87) PCT Pub. No.: WO2014/124532
PCT Pub. Date: Aug. 21, 2014

(65) Prior Publication Data
US 2015/0377769 A1    Dec. 31, 2015

Related U.S. Application Data

(60) Provisional application No. 61/764,914, filed on Feb. 14, 2013.

(51) Int. Cl.
*G01J 3/28* (2006.01)
*G01N 21/27* (2006.01)
(Continued)

(52) U.S. Cl.
CPC ......... *G01N 21/278* (2013.01); *G01N 21/645* (2013.01); *G01N 21/65* (2013.01);
(Continued)

(58) Field of Classification Search
CPC ........ G01N 21/27; G01N 21/64; G01N 21/65; G01J 3/02; G01J 3/28; G01J 3/44
See application file for complete search history.

(56) References Cited

U.S. PATENT DOCUMENTS

2005/0079628 A1* 4/2005 Nekrasov ............... G01N 21/31
436/164

\* cited by examiner

Primary Examiner — Abdullahi Nur

(57) ABSTRACT

Examples of an optical standard and a calibration apparatus for calibrating or characterizing a spectroscopy system using such optical standard are disclosed. The optical standard can comprises a mixture of acetaminophen and barium sulfate, wherein a mass of the acetaminophen in the mixture is being less than a mass of the BaSO4. Such optical standard can be used in a calibration device for calibrating or characterizing a spectroscopy system. The calibration device can comprise a substrate base with a top surface and a bottom surface. The top surface can include a section for receiving the optical standard sample. The receiving section can be adhesive. The calibration device can further comprise a film that can be attached to the top surface of the substrate base to cover at least the section of the substrate where the optical standard is being placed. The calibration device can be disposed after the calibration measurements are completed. The optical standard and the calibration apparatus using the optical standard can be used as a wavelength calibration standard to calibrate a Raman system, a reflectance reference standard for a reflectance spectral measurement or for a reliability check in a fluorescence spectral system.

11 Claims, 8 Drawing Sheets

(51) Int. Cl.
  *G01N 21/65* (2006.01)
  *G01N 21/64* (2006.01)
  *A61B 5/00* (2006.01)
(52) U.S. Cl.
  CPC ..... *A61B 5/0075* (2013.01); *A61B 2560/0233* (2013.01); *G01N 2021/6482* (2013.01)

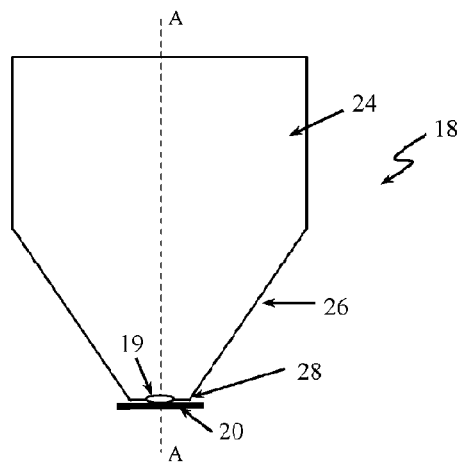
FIG. 7
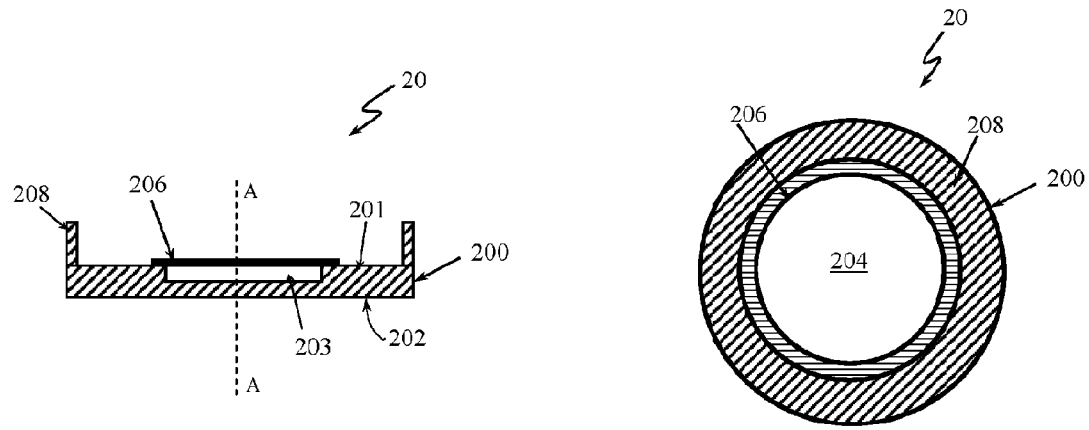
FIG. 8a                    FIG. 8b

OPTICAL STANDARD FOR CALIBRATION OF SPECTRAL MEASURING SYSTEMS

TECHNICAL FIELD

The present invention relates generally to an optical standard for calibration or characterization of optical measuring devices and as a reference system for intensities and intensity measurements and more particular relates to an optical standard for calibration of spectra measuring instruments and spectral measuring systems using such optical standard.

BACKGROUND

The use of optical measuring devices, for example, in real-time detection, diagnosis and imaging of diseases can require a regular calibration and characterization of such optical measuring devices. The calibration of optical measuring systems can be effected with standards, such as, for example, certified radiation-intensity-per-unit-area standards or a spectrally corrected standards where an instrument-independent emission and/or scatter spectra can be used. The availability of such standards is very important for the long-term instrument stability and reliability.

Generally speaking, the measurement of reflectance or fluorescence or Raman signals plays a great role in biomedical applications, for example for the early diagnosis of disease-specific changes on the molecular level. American Society for Testing and Materials (ASTM) has established a series of Raman shift frequency standards (ASTM E 1840) that can be used in calibration of Raman spectrometers. Typically, Raman shifts frequencies of the following compounds are included in the standard: Naphthalene; benzene; sulfur; toluene; acetaminophen; benzonitrile; cyclohexane; and polystyrene.

Spectroscopy systems such as a Raman spectroscopy system or fluorescence spectrometer can be limited by a poor signal to noise ratio which may impede the spectral measurements and reliability of such measurements especially for in vivo real time medical procedures. The low signal to noise ratio is a consequence of the low strength or absence of an optical signal coming from the target tissue, a high level of background noise and poor sensitivity and specificity of the detected optical signal.

Therefore, there is a need for reliable, accurate and simple method and apparatus for calibration, characterization and reliability check of the spectral measuring systems such as Raman, fluorescence and reflectance spectroscopy systems for a long-term system stability and reliability.

SUMMARY

In one aspect, an optical standard for calibrating a spectroscopy probe is provided. The optical standard for the calibration or characterization of the spectroscopy probe can comprises a mixture of acetaminophen and barium sulfate. The amount of acetaminophen in the mixture is less than the amount of barium sulfate. The optical standard can be used as a wavelength calibration standard to calibrate a Raman system.

In another aspect, the optical standard can be used as a reflectance reference standard for a reflectance spectral measurement or for a reliability check in a fluorescence spectral system.

In one aspect, an apparatus for calibrating or characterizing a spectroscopy probe is provided. The apparatus can comprise a substrate base with a top surface and a bottom surface. The top surface can include a section for receiving an optical standard sample. The receiving section can be adhesive. The standard sample can comprise a mixture of acetaminophen and barium sulfate where a mass of the acetaminophen is less than a mass of the barium sulfate. The calibration apparatus can be disposed after the calibration measurements are completed. The calibration apparatus can further comprise a film that can be attached to the top surface of the substrate base. The film can be dimensioned to cover at least the section of the substrate where the optical standard is being placed.

In another aspect, a spectroscopy probe is provided. The spectroscopy probe can comprise a tip mounted at a distal end of the probe. The tip comprises an opening through which an illumination light beam and a returning radiation can pass. A disposable calibration strip can be attached to the tip to cover the opening of the tip. The calibration strip can comprise an optical calibration standard for calibrating the spectroscopy probe. The calibration strip can be removable once the spectroscopy probe is being calibrated.

In one aspect, the calibration strip can be disposable once the spectroscopy probe is being calibrated.

In yet another aspect, the probe's tip can be removable and disposable once the spectral measurements have been completed.

In another aspect, a method for calibrating a spectroscopy probe is provided using an optical standard.

In addition to the aspects and embodiments described above, further aspects and embodiments will become apparent by reference to the drawings and study of the following detailed description.

BRIEF DESCRIPTION OF THE DRAWINGS

Throughout the drawings, reference numbers may be re-used to indicate correspondence between referenced elements. The drawings are provided to illustrate example embodiments described herein and are not intended to limit the scope of the disclosure. Sizes and relative positions of elements in the drawings are not necessarily drawn to scale. For example, the shapes of various elements and angles are not drawn to scale, and some of these elements are arbitrarily enlarged and positioned to improve drawing legibility.

FIG. 7 is a side view of an example of a distal tip of a spectroscopy probe.

FIG. 8a is a side view of a calibration apparatus of the present invention.

FIG. 8b is a top view of the calibration apparatus of FIG. 8a.

DETAILED DESCRIPTION OF SPECIFIC EMBODIMENTS

Figure 1:
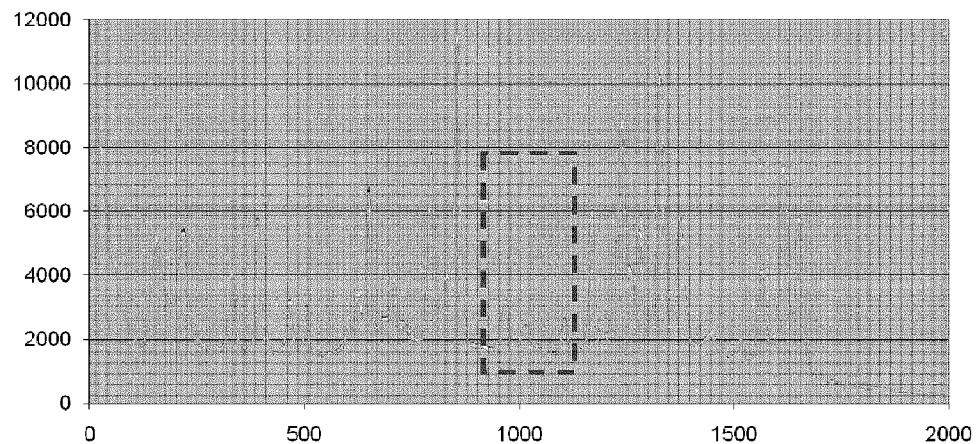
FIG. 1 is a graphical illustration of output spectra of an acetaminophen measured within 1 s integration time.

An acetaminophen is an active ingredient of a well-known drug for reducing pain or fever selling under trademark TYLENOL™. The acetaminophen is a non-toxic compound that can be purchase as a powder and according to ASTM it can be used as standard for calibrating Raman spectrometers. FIG. 1 illustrates raw spectra of the acetaminophen measured with a 1 s integration time. As can be noticed there are a lot of peaks in a region of 500-1800 cm$^{-1}$ however, there are no strong peaks around 1000 cm$^{-1}$ (see peaks shown within a dashed lined square) which is of great interest for the Raman spectral measurements.

Figure 2:
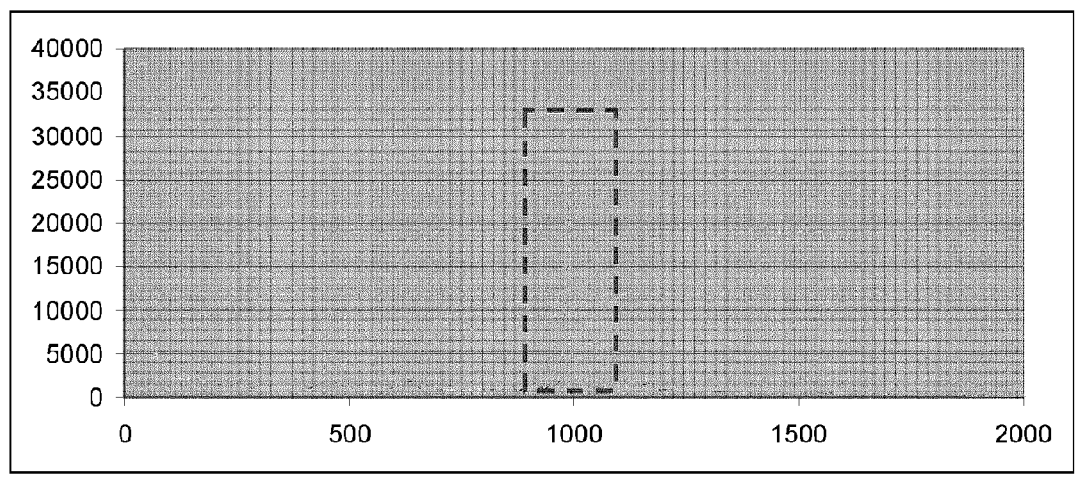
FIG. 2 is a graphical illustration of output spectra of a barium sulfate (BaSO4) measured within 1 s integration time.

The applicants have conducted a number of experiments and have found that raw spectra of barium sulfate (BaSO4) (see FIG. 2) have a strong peak around 1000 cm$^{-1}$ (see peak shawn within a dashed lined square). BaSO4 is a compound with relatively stable chemical properties and it is non-toxic. Unfortunately, the spectra of BaSO4 have no other strong peaks in the region of 500-1800 cm$^{-1}$.

Figure 3A:
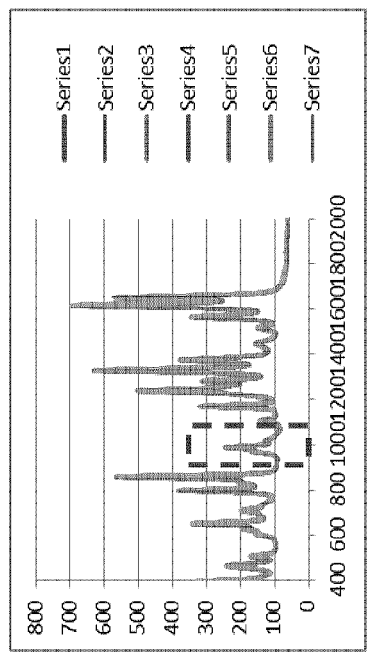
FIGS. 3a-3d illustrate output spectra for a number of acetaminophen and BaSO4 mixtures with various mass ratios of the acetaminophen and BaSO4.
Figure 3B:
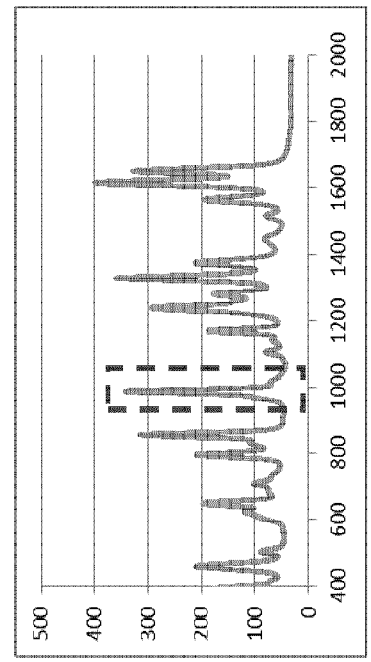
Figure 3C:
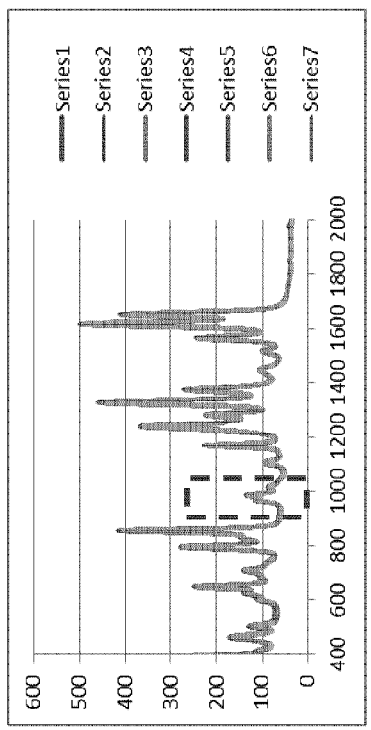
Figure 3D:
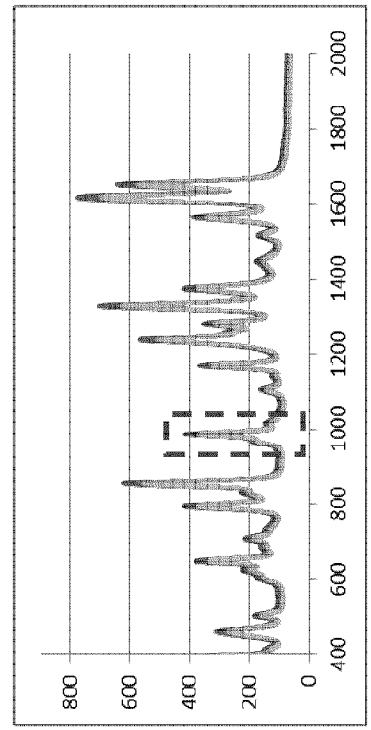

Further experiments have been conducted using a number of mixtures of acetaminophen and barium sulfate. FIGS. 3a to 3d illustrate graphs of raw spectra (1 s integration time) for a number of acetaminophen and BaSO4 mixture. The dashed lined square in each of FIGS. 3a to 3d shows the region of interest for Raman spectral measurements. FIGS. 3a and 3b show the spectra of various mixtures of acetaminophen and BaSO4 where the mass of the acetaminophen in the mixture is higher than the mass of the BaSO4. FIG. 3c shows the spectra of acetaminophen and BaSO4 mixture with mass ratio of about 1 to 1. As can be noticed in all of these examples (FIGS. 3a to 3c) the peak close to 1000 cm$^{-1}$ is still quite weak although the signal in FIG. 3c has a stronger peak comparing to the signal shown in FIGS. 3a and 3b. The experiments have shown the best results with a mixture of acetaminophen and BaSO4 where the mass of the acetaminophen in the mixture is less than the mass of the BaSO4 as illustrated in FIG. 3d. FIG. 3d shows the spectra with a strong peak close to 1000 cm$^{-1}$ region.

More experiments have been conducted to assess the compatibility of the acetaminophen and BaSO4 mixture with a mass of the acetaminophen in the mixture being less than a mass of the BaSO4 (herein further called standard mixture) for use as a calibration standard for calibrating spectroscopy systems. For example, the ratio of the acetaminophen to BaSO4 in the standard mixture can be 1:2, 1:3, 1:4 or 1:5 or any other suitable ratio where the mass of the acetaminophen is less than the mass of the BaSO4.

Figure 4:
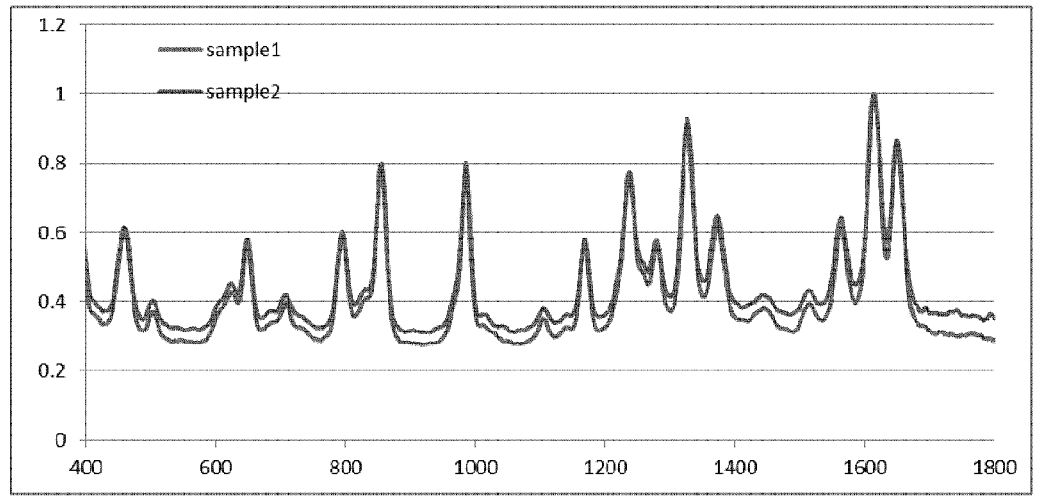
FIG. 4 is a graph of Raman measurements of a small diameter standard sample.

First it was assessed whether a small diameter of sample of standard mixture can provide a good spectral signal. The size of the sample standard can be important to match a size of a distal tip of a spectroscopy probe. A solution of acetaminophen and BaSO$_4$ in distilled water (mass of the acetaminophen being less than the mass of the BaSO4) has been prepared and a droplet of 2 mm of such solution has been provided to an aluminum foil. After the droplet has dried (water evaporated) and the solid mixture is firmly settled on the aluminum foil, the Raman signal has been measured. The results of the Raman measurements of two samples of 2 mm droplets of standard mixture are illustrated in FIG. 4. As can been noticed from the graphs of FIG. 4 the small diameter sample can provide a good Raman signals.

Figure 5:
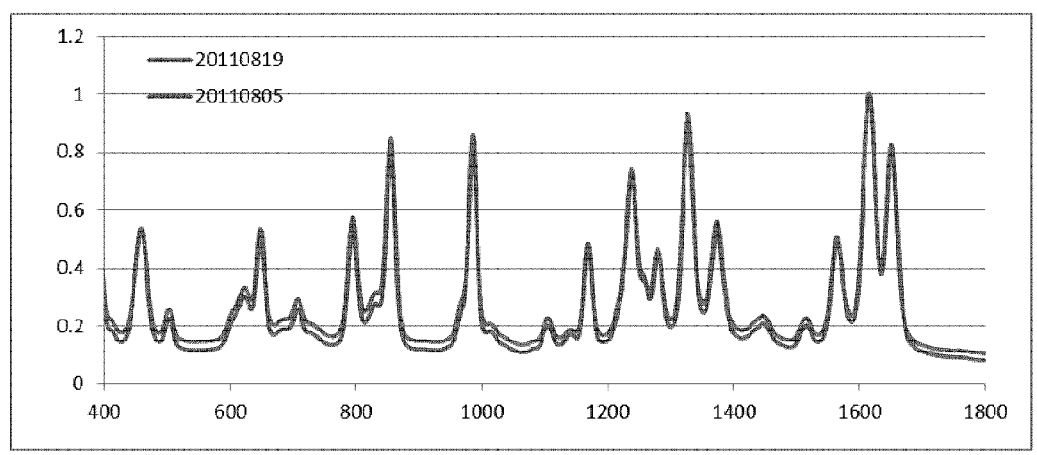
FIG. 5 is a graph of Raman measurements of the standard sample to test the sample stability over time.

The applicant has further tested sample stability over time to confirm that the standard mixture of acetaminophen and BaSO4 can be used as calibration standard for spectral measuring probes. FIG. 5 shows a Raman signal of a sample that was prepared on Aug. 2, 2011. First Raman measurements were taken on Aug. 5, 2011 and then again on Aug. 19, 2011. As can be noticed in case of spectra measured of the same sample at two different days (two weeks apart), the Raman signal is similar proving that the standard mixture can be stable at least for 15 days and possibly even longer.

Figure 6:
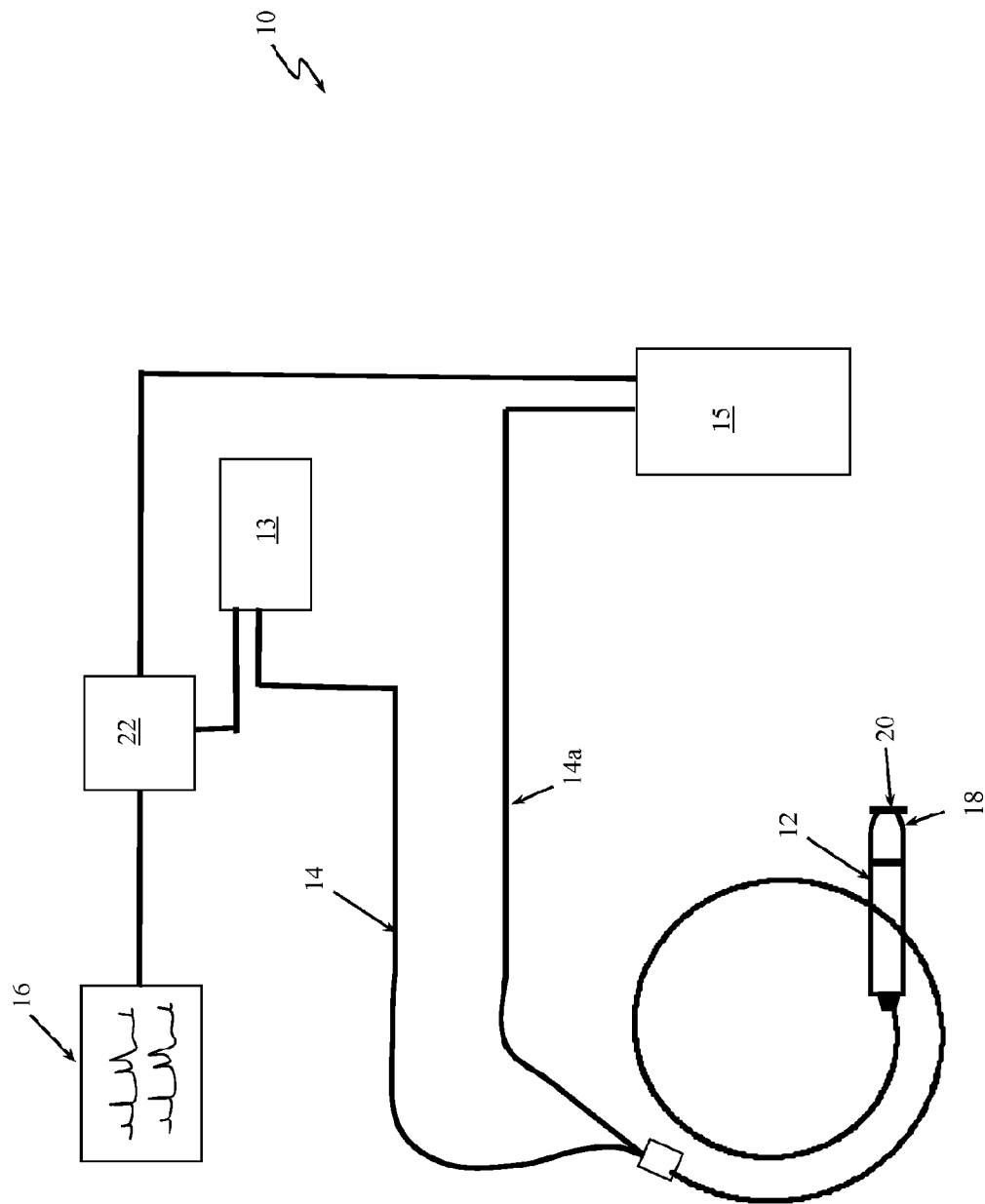
FIG. 6 schematically illustrates a spectroscopy system that can be calibrated using calibration apparatus of the present invention.

FIG. 6 schematically illustrates a spectroscopy system 10 with a spectroscope probe 12 that can be calibrated using the optical standard (standard mixture) described previously herein. The spectroscopy system 10 can be a Raman spectroscopy system, a reflectance spectroscopy system or fluorescence spectroscopy system or a combination thereof. The spectroscopy system 10 can comprise a light source 13 to provide an illumination light. The light source 13 can be one or more lamp, light emitting diode (LED), laser or any other light source or combinations of light sources suitable for use with spectroscopy systems. The light source 13 can be placed outside the spectroscopy probe 12 and the produced illumination light beam can be focused into a light guide 14 and can be transmitted to the probe 12 and a subject under examination. Radiation returning (reflected or emitted light) from the subject can be focused into a light guide 14a and can be directed to a detector such as a spectrometer 15. In one implementation, the illumination light can be directed to the subject and the returning radiation can be directed to the detector 15 using the same light guide. In another implementation, the light source 13 can be located within the spectroscopy probe 12 in proximity to a distal tip 18. The signal from the detector 15 can be displayed on a monitor 16.

The distal tip 18 can comprise an opening 19 (FIG. 7) that can be configured to pass the illumination light to the subject and to allow the radiation returning from the subject to be directed to the detector 15. The distal tip 18 can be a contact tip configured to be brought into contact with the subject under examination or a non-contact in case when the spectral measurements are taken with a non-contact spectroscopy probe. A strip 20 comprising a standard mixture of acetaminophen and BaSO4 can be placed on the distal tip 18 to cover the opening 19 of the tip.

FIG. 7 is a side view of the distal tip 18 of the probe 12 showing the tip 18 in more details. The tip 18 comprises a body 24 with a head 26. The head 26 can be tapered toward a point end 28. The opening 19 can be formed at the point end 28. In one embodiment, the point end 28 can have a flat surface. A diameter of the opening 19 can be slightly smaller of a diameter of the point end 28 of the tip 18. The strip 20 can be adhered to the point end 28 of the tip 18 to cover the opening 19.

FIGS. 8a and 8b shows in details the strip 20. FIG. 8a is a side view of the strip 20 and FIG. 8b is a top view of the strip 20. The strip is dimensioned and designed to act as a calibration device for calibrating the spectroscopy probe 12. The strip 20 can have a substrate base 200 with a top surface 201 and a bottom surface 202. The substrate base 200 can have a rectangular, a circular or any other form suitable to be placed over the end 28 of the distal tip 18. The substrate base 200 can further comprise a section 203 configured to receive the standard mixture of acetaminophen and BaSO$_4$.

The section 203 can be an indentation formed in the top surface 201 of the substrate base 200 so that when a sample of the standard mixture 204 (see FIG. 8b) is placed in the indentation 203 the top surface of the standard can level with the top surface 201 of the substrate base 200. The indentation 203 can prevent the standard mixture to slip out of the substrate base 200. The substrate base 200 can be an aluminium foil, a black aluminium foil, a paper or any other suitable material. In one implementation, the section 203 for receiving the standard sample 204 can be adhesive to fix the sample on the base substrate 200. The adhesive receiving section 203 can prevent the sample 204 to slip out of the base substrate 200. For example, an adhesive tape can be used as adhesive section 203. The sample 204 can be put on a sticky side of the tape 203 and then the tape can be placed onto the substrate base 200. In one implementation, a double sided adhesive tape can be used for receiving section 203. In one embodiment a black paper tape can be used. This is only for illustrative purposes and the receiving section 203 can have any other design that can provide secure fixing of the standard sample 204 onto the receiving section 203 without departing from the scope of the invention. The strip 20 can further comprise a film 206 that can be put over the sample 204 to cover it. The film can prevent the standard sample to interfere with the distal tip 18 of the probe 12 and thus contaminate the distal tip 18 and indirectly the subject under examination. The film 206 can be any suitable plastic film such as a polyvinyl or a polyethylene film. The film 206 should be sized to cover the standard sample 204 and or the receiving section 203. The strip 20 can further comprise adhesive side 208 formed at the edge of the base 200 and extending from the base 200. The adhesive side 208 comprises a bonding agent, such as glue, to allow the strip 20 to be attached to the head 26 at the side of the distal end 28. By gluing the strip 20 to the side of the end 28, any residue of the glue that can contaminate the end 28 of the probe and/or the subject of the examination can be prevented and thus any compromise of the spectral measurements can be avoided. Person skilled in the art would understand that any other bonding agent or connecting method can be used to attach the strip 20 to the distal tip 18 without departing from the scope of invention. For example, the bonding agent can be placed at the head 26 of the distal tip 18. The bonding agent should be placed away of the opening 19 to avoid contamination of the light guides 14, 14a. A channel (not shown) can be formed on the end 28 of the distal tip 18 around the opening 19. This channel can act as a "glue run off" channel to prevent the glue to reach the opening 19 and/or the light guides 14, 14a. In one implementation the opening 19 can be a window, such as for example a quartz window (or any other material with low Raman and fluorescence background).

Figure 9:
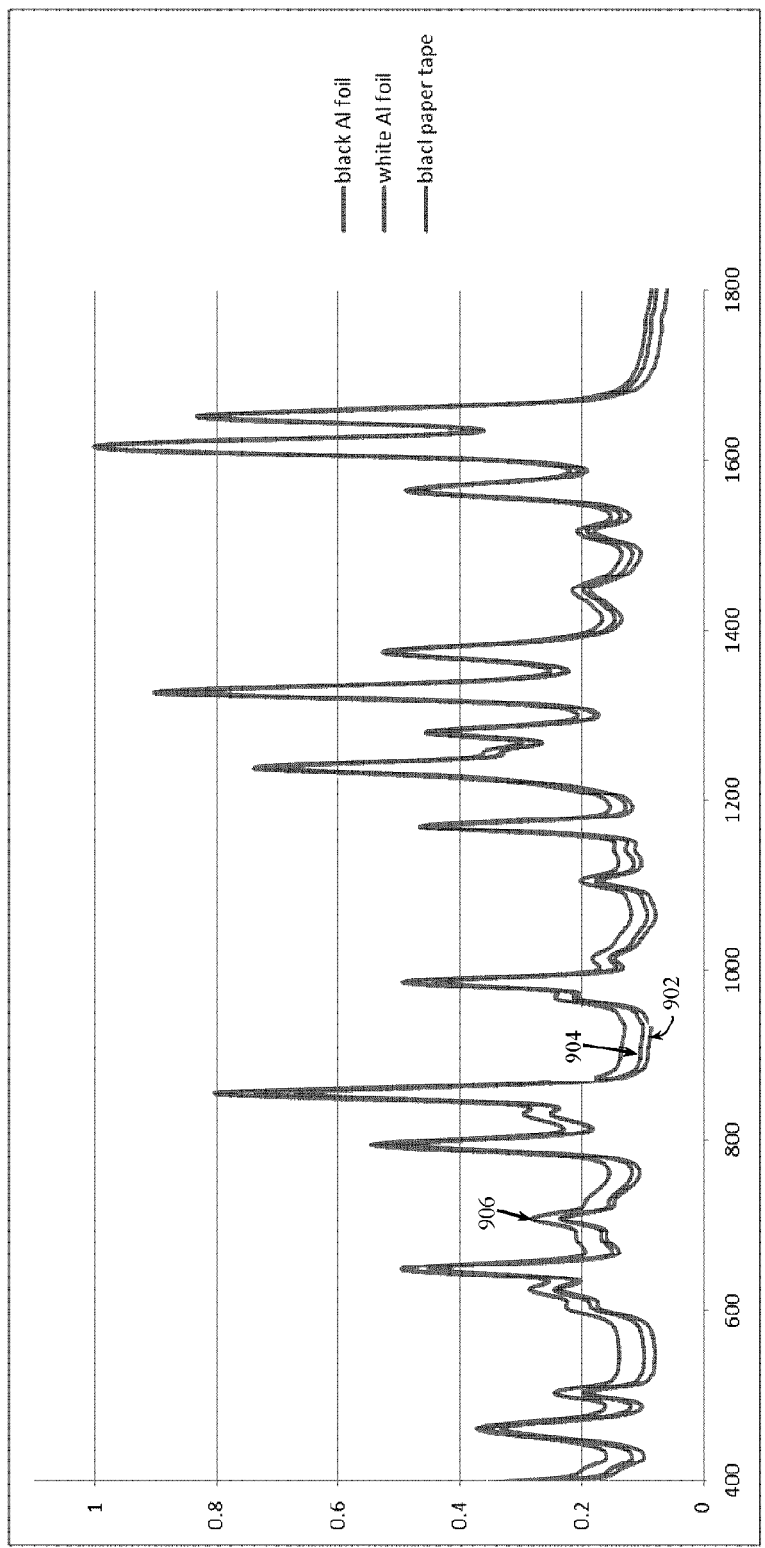
FIG. 9 graphically illustrates a Raman signal of a standard sample when placed at three different substrate bases.

The material of the substrate base 200 and/or the receiving section 203 should have a minimum effect on the spectrum of the optical standard 204. For example, FIG. 9 illustrates a Raman signal of the standard mixture when placed at three different substrate bases such as, a black aluminum foil (curve 902), a white aluminum foil (curve 904) and a black paper tape (curve 906). As can be noticed from the graphs any of the tested materials have a minimum background noise. Some of the tested materials can have some fluorescence background but such noise is acceptable. Peaks from the sample can still be well differentiated from the background and the Raman spectra of the standard sample can be extracted.

Figure 10:
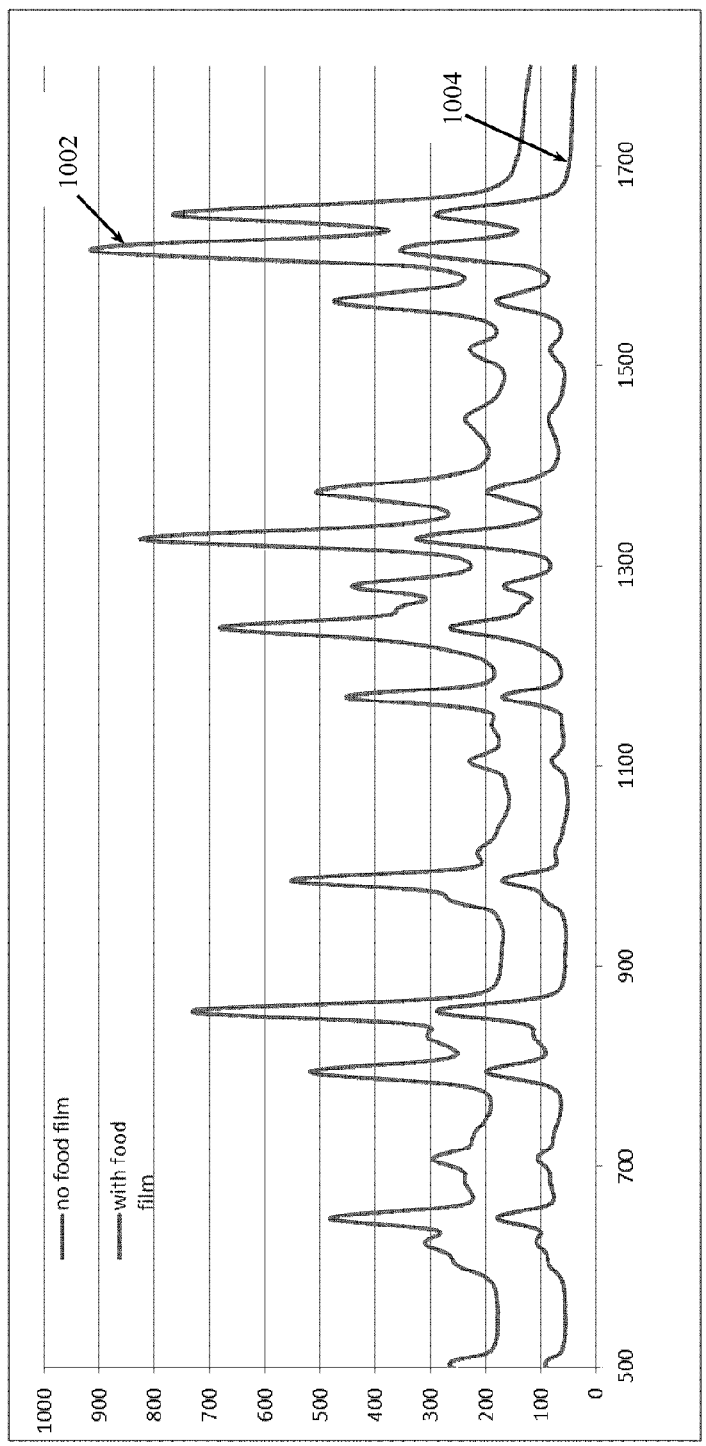
FIG. 10 graphically illustrates Raman spectra of the standard sample with no cover film (curve 1002) and with a cover film (curve 1004) over the standard sample.

FIG. 10 shows Raman spectra of the standard sample 204 with no film 206 covering the sample (curve 1002) and Raman spectra of the same standard sample 204 with a film 206 placed over the sample (curve 1004). As can be noticed from the graphs of FIG. 10, the film 206 does not affect the Raman signal from the standard sample 204. The experiments have also shown that if the standard sample 204 is large and/or thick, fluorescence background signal from the substrate base 200 and/or the receiving section 203 can be further minimized.

In one method of operation, the calibration strip 20 can be attached to the distal tip 18 to cover the opening 19. Before the beginning of the spectral measurements from the subject under examination, the spectroscopy system 10 (FIG. 6) can be switch on and a spectra from the standard sample 204 placed on the calibration strip 20 can be measured to calibrate or check reliability of the probe 12 and/or the system 10. Once the probe 12 and/or system 10 is calibrated the strip 20 can be removed from the distal tip 18 and disposed and a spectra from the subject under examination can be measured. In one implementation, a reusable calibration strip can be used.

Figure 11:
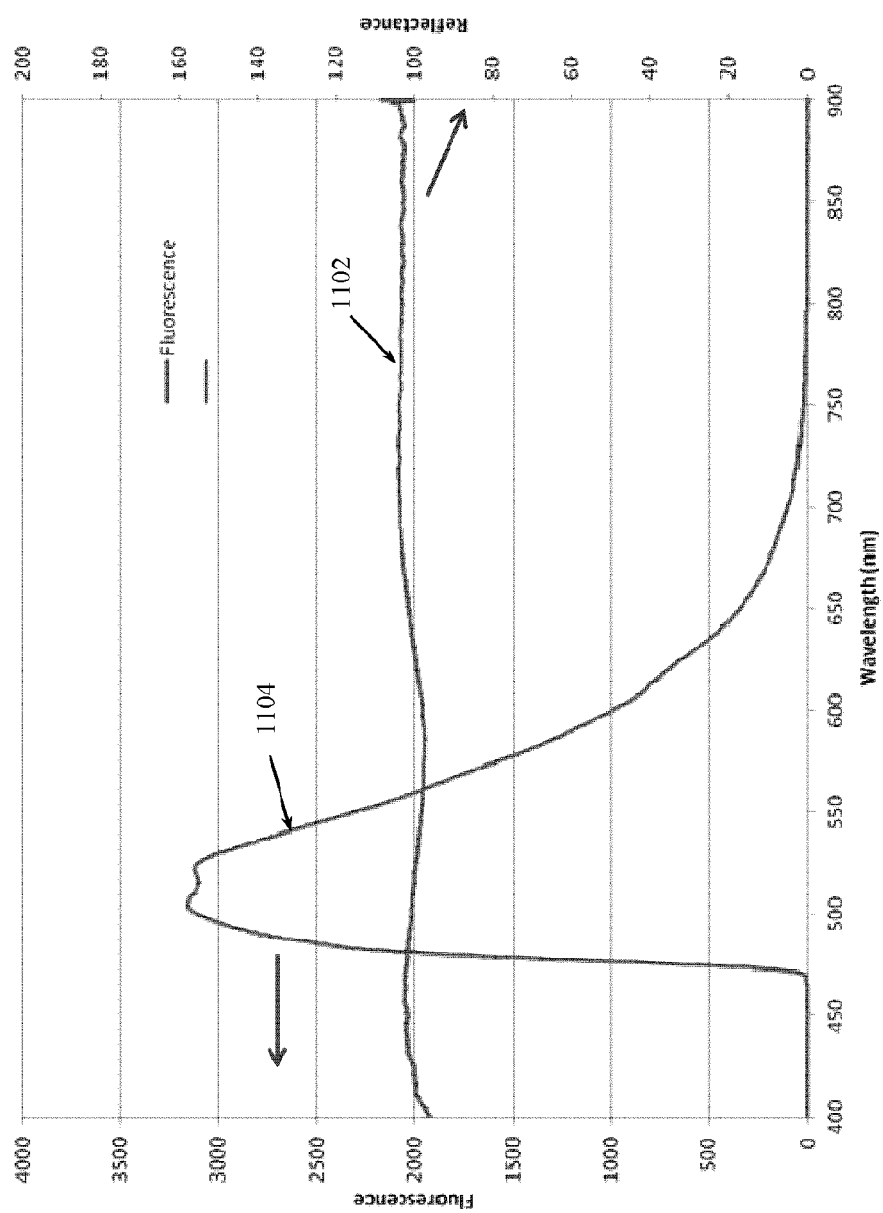
FIG. 11 graphically illustrates a reflectance spectrum (curve 1102) and a fluorescence spectrum (curve 1104) measured from a standard sample.

Embodiments of the calibration apparatus (e.g. the calibration strip 20) and the optical standard 204 can also be used as a reflectance reference standard for reflectance spectral measurements and to check the reliability of a fluorescence spectrometer. FIG. 11 shows a reflectance spectrum (curve 1102) and fluorescence spectrum (curve 1104) measured from the standard 204 placed on the calibration strip 20. It has been shown that the calibration strip 20 can have a flat close to 100% reflectivity in the visible and near infrared wavelength range and thus can be suitable as a reflectance reference standard. The fluorescence signal (curve 1104) is also strong enough so it can be used to check reliability of the fluorescence spectroscopy system.

While particular elements, embodiments and applications of the present disclosure have been shown and described, it will be understood, that the scope of the disclosure is not limited thereto, since modifications can be made without departing from the scope of the present disclosure, particularly in light of the foregoing teachings. Thus, for example, in any method or process disclosed herein, the acts or operations making up the method/process may be performed in any suitable sequence and are not necessarily limited to any particular disclosed sequence. Elements and components can be configured or arranged differently, combined, and/or eliminated in various embodiments. The various features and processes described above may be used independently of one another, or may be combined in various ways. All possible combinations and subcombinations are intended to fall within the scope of this disclosure. Reference throughout this disclosure to "some embodiments," "an embodiment," or the like, means that a particular feature, structure, step, process, or characteristic described in connection with the embodiment is included in at least one embodiment. Thus, appearances of the phrases "in some embodiments," "in an embodiment," or the like, throughout this disclosure are not necessarily all referring to the same embodiment and may refer to one or more of the same or different embodiments. Indeed, the novel methods and systems described herein may be embodied in a variety of other forms; furthermore, various omissions, additions, substitutions, equivalents, rearrangements, and changes in the form of the embodiments described herein may be made without departing from the spirit of the inventions described herein.

Various aspects and advantages of the embodiments have been described where appropriate. It is to be understood that not necessarily all such aspects or advantages may be achieved in accordance with any particular embodiment.

Thus, for example, it should be recognized that the various embodiments may be carried out in a manner that achieves or optimizes one advantage or group of advantages as taught herein without necessarily achieving other aspects or advantages as may be taught or suggested herein.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without operator input or prompting, whether these features, elements and/or steps are included or are to be performed in any particular embodiment. No single feature or group of features is required for or indispensable to any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

Conjunctive language such as the phrase "at least one of X, Y and Z," unless specifically stated otherwise, is otherwise understood with the context as used in general to convey that an item, term, etc. may be either X, Y or Z. Thus, such conjunctive language is not generally intended to imply that certain embodiments require at least one of X, at least one of Y and at least one of Z to each be present.

The example calculations, simulations, results, graphs, values, and parameters of the embodiments described herein are intended to illustrate and not to limit the disclosed embodiments. Other embodiments can be configured and/or operated differently than the illustrative examples described herein. Indeed, the novel methods and apparatus described herein may be embodied in a variety of other forms; furthermore, various omissions, substitutions and changes in the form of the methods and systems described herein may be made without departing from the spirit of the inventions disclosed herein.

The invention claimed is:

1. A calibrating device for calibrating or characterizing a spectral measuring system, the device comprising:
   a substrate base having a top surface and a bottom surface, the base being configured to be detachably placed to a distal end of a spectral probe; and
   a receiving section positioned at the top surface of the substrate base for receiving an optical standard, the receiving section configured to fix the optical standard thereto, the receiving section configured to cover the distal end of the probe when the base is placed to the end of the probe,
   wherein the optical standard comprises a mixture of an acetaminophen and a barium sulfate, wherein a mass of the acetaminophen is being less than a mass of the barium sulfate.

2. The calibrating device of claim 1, further comprising a cover sized to protect the optical standard and the receiving section.

3. The calibrating device of claim 1, wherein the substrate base comprises a lip extending from an edge of the base configured to be detachably placed to a side wall of the distal tip such that the receiving section covers the distal end of the probe.

4. The calibrating device of claim 1, wherein the substrate base is selected from a group comprising a black aluminum foil, white aluminum foil and black paper tape.

5. The calibrating device of claim 1, wherein the device is reusable.

6. The calibrating device of claim 1, wherein a ratio of the acetaminophen and the barium sulfate is 1:2.

7. A spectroscopy probe with a detachable calibration device, the probe comprising:
   a housing having a proximate end and a distal end and longitudinal axis between the proximate end and the distal end;
   at least one light source for generating illumination light beam;
   means for receiving the illumination beam from said at least one light source and for directing it toward an object under examination;
   means for receiving a returning radiation from the object and directing at least part of the returning radiation to a detector;
   a head position at the distal end of the probe having a body and a tapering tip, an opening formed at the tip of the head for the illumination light beam and the returning radiation to pass there through; and
   a detachable calibration device attached to the tip of the head to cover the opening, the calibration device comprising an optical standard with a mixture of an acetaminophen and a barium sulfate, wherein a mass of the acetaminophen is being less than a mass of the barium sulfate.

8. The spectroscopy probe of claim 7, wherein the head of the probe being removable and disposable.

9. The spectroscopy probe of claim 7, further comprising a grooved channel formed at the tip, the channel extending around the opening.

10. The spectroscopy probe of claim 7, wherein a ratio of the acetaminophen and the barium sulfate is 1:2.

11. A method for the spectral calibration or characterization of a spectral measuring system comprising the steps of:
    providing a calibration device with an optical standard comprising a mixture of an acetaminophen and barium sulfate at a tip of the spectral system;
    measuring spectra from the optical standard to calibrate or characterize the spectral system;
    removing the calibration device from the tip of the spectral system, and
    measuring spectra from a subject of interest.

* * * * *